US010973986B2

(12) United States Patent
Fournier et al.

(10) Patent No.: US 10,973,986 B2
(45) Date of Patent: Apr. 13, 2021

(54) PROTECTIVE DEVICE FOR A SYRINGE NEEDLE

(71) Applicant: APTAR STELMI SAS, Villepinte (FR)

(72) Inventors: Ghislain Fournier, La Rochelle (FR); Mickael Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 0 days.

(21) Appl. No.: 15/027,894

(22) PCT Filed: Oct. 6, 2014

(86) PCT No.: PCT/FR2014/052521
§ 371 (c)(1),
(2) Date: Apr. 7, 2016

(87) PCT Pub. No.: WO2015/052417
PCT Pub. Date: Apr. 16, 2015

(65) Prior Publication Data
US 2016/0271338 A1    Sep. 22, 2016

(30) Foreign Application Priority Data
Oct. 8, 2013   (FR) ...................................... 1359754

(51) Int. Cl.
*A61M 5/32*      (2006.01)
*A61M 5/00*      (2006.01)
*A61M 5/31*      (2006.01)

(52) U.S. Cl.
CPC ............ *A61M 5/3202* (2013.01); *A61M 5/001* (2013.01); *A61M 2005/3103* (2013.01)

(58) Field of Classification Search
CPC ........ A61M 5/001; A61M 5/50; A61M 5/626; A61M 5/3202; A61M 5/3213;
(Continued)

(56) References Cited

U.S. PATENT DOCUMENTS 4,240,427 A * 12/1980 Akhavi ............... A61M 5/3202
604/263
4,915,699 A * 4/1990 Kornberg ............ A61M 5/3243
604/195
(Continued)

FOREIGN PATENT DOCUMENTS

EP    0 429 052 A1    5/1991
EP    0 592 814 A2    4/1994
(Continued)

OTHER PUBLICATIONS

International Preliminary Report on Patentability for PCT/FR2014/052521, published on WIPO Patentscope on Feb. 16, 2016.
(Continued)

*Primary Examiner* — Shefali D Patel
*Assistant Examiner* — Tezita Z Watts
(74) *Attorney, Agent, or Firm* — Sughrue Mion, PLLC

(57) ABSTRACT

A protection device for a syringe needle, having an elastomeric cap. The cap defining a housing receiving the distal portion of the body of a needle syringe. An end wall of the cap perforatable over a fraction of its thickness by the free end of the needle. The housing having a first segment of frustoconical or cylindrical shape; a cylindrical second segment for housing the distal portion of the syringe body that carries the needle, and a third segment that tapers from the second segment towards the end wall of the housing, the lateral wall provided with an annular bead arranged in the housing, at least one slot extending in a longitudinal direction across the annular bead. The second segment includes at least one axial groove that extends longitudinally over a fraction of the height of the second segment.

19 Claims, 2 Drawing Sheets

(58) Field of Classification Search
CPC .. A61M 5/3216; A61M 5/3243; A61M 5/322;
A61M 2005/3103; A61M 2005/3107;
A61M 2005/3109; A61M 2005/311;
A61M 2005/312; A61M 2005/3223;
A61M 2005/3224; A61M 2005/3226;
A61M 2005/323; A61M 2005/3231
See application file for complete search history.

(56) References Cited

U.S. PATENT DOCUMENTS

| | | | | |
|---|---|---|---|---|
| 5,607,400 | A | * | 3/1997 | Thibault ........... A61M 5/31513 604/218 |
| 2002/0062108 | A1 | * | 5/2002 | Courteix ............. A61M 5/3202 604/198 |
| 2003/0018303 | A1 | * | 1/2003 | Sharp ................... A61M 5/3202 604/192 |
| 2007/0250016 | A1 | * | 10/2007 | Pech ................... A61M 5/3213 604/198 |
| 2015/0217061 | A1 | * | 8/2015 | Sadowski ........... A61M 5/3202 604/192 |

FOREIGN PATENT DOCUMENTS

| | | |
|---|---|---|
| EP | 0 976 415 A2 | 2/2000 |
| EP | 1 099 450 A1 | 5/2001 |
| EP | 1 208 861 A1 | 5/2002 |
| FR | 2 913 200 A1 | 9/2008 |

OTHER PUBLICATIONS

International Search Report of PCT/FR2014/052521 dated Feb. 23, 2015.

* cited by examiner

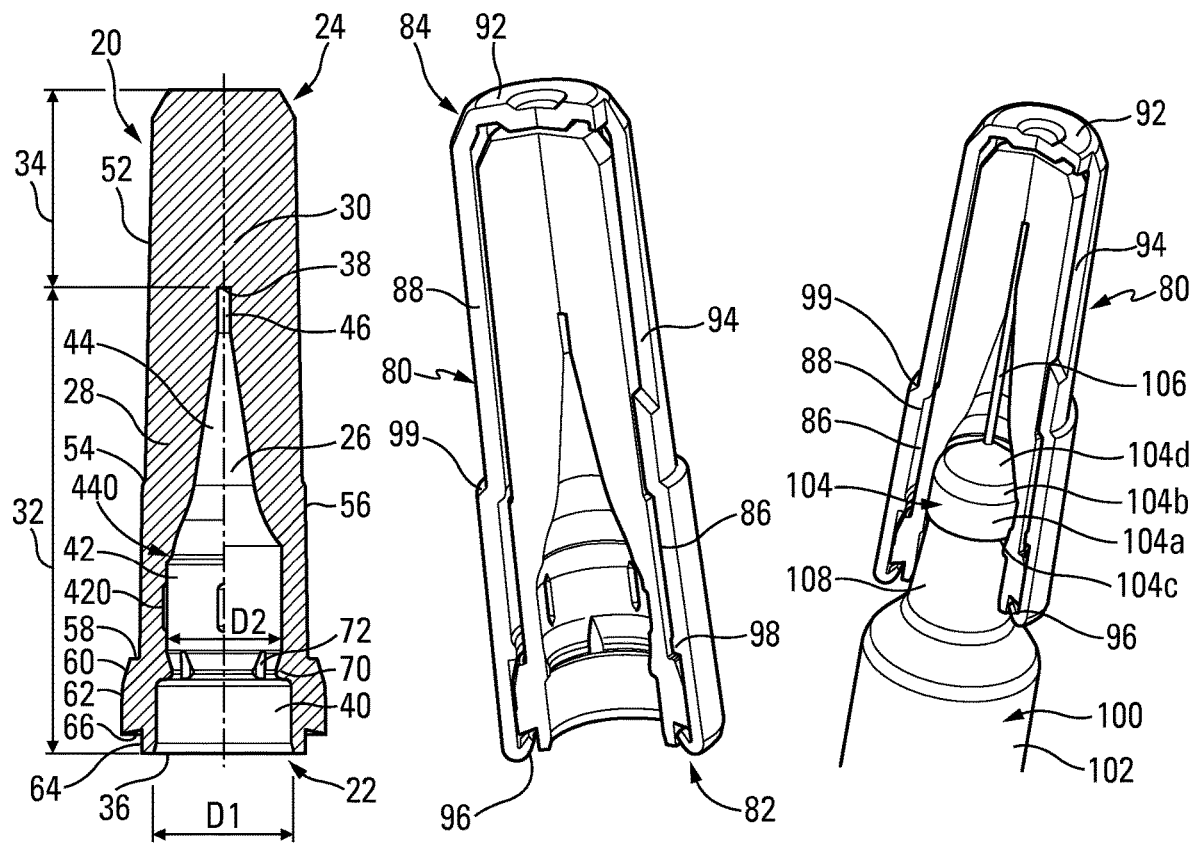
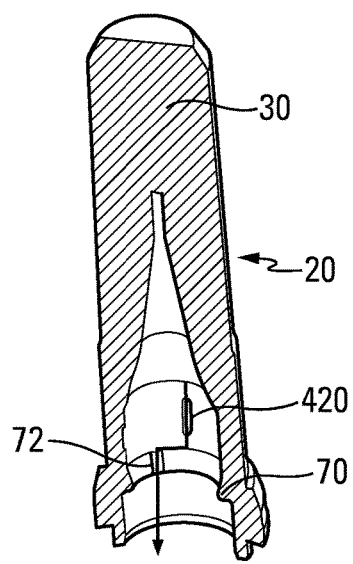

PROTECTIVE DEVICE FOR A SYRINGE NEEDLE

CROSS REFERENCE TO RELATED APPLICATIONS

This application is a National Stage of International Application No. PCT/FR2014/052521 filed Oct. 6, 2014 claiming priority based on French Patent Application No. 1359754, filed Oct. 8, 2013, the contents of which are incorporated herein by reference in their entirety.

The present invention relates to a syringe-needle protection device comprising an elastomeric needle cap.

More precisely, the present invention relates to a protection device for protecting a syringe needle, which device is of the type that comprises an elastomeric needle cap that extends in a generally longitudinal direction and that has a closed distal end and an open proximal end, said cap being formed by a lateral wall that extends from said proximal end along a proximal end zone, defining an internal housing for receiving the distal portion of the body of a needle syringe, and by an end wall having a thickness that extends from said distal end along a distal end zone, said end wall being suitable for being perforated over a fraction of its thickness by the free end of said needle, the housing comprising, from said proximal end: an opening that presents a maximum diameter; a first segment of frustoconical or circularly cylindrical shape; a circularly-cylindrical second segment that presents a diameter that is less than the maximum diameter, and that is for housing the distal portion of the syringe body that carries said needle; and a third segment that tapers from the second segment to the end wall of said housing.

Protection devices for protecting a syringe needle of the above-mentioned type have already been proposed.

Thus, patent EP 0 429 052 relates to a needle shield assembly comprising an elastomeric needle sheath similar to the above-defined elastomeric needle cap.

However, that type of needle protection device presents a certain number of drawbacks.

The syringe-needle protection device that is the subject of the present invention is for mounting on a hypodermic syringe that enables a medicated liquid to be injected into a patient.

Regardless of whether the hypodermic syringes are pre-filled or they are filled by hospital personnel just before performing the injection, it is necessary for the syringe to remain sterile until it is used.

For example, when the syringe is packaged when already pre-filled with liquid, the following various steps are performed in order to prepare the syringe before it is packaged. Initially, the body of the syringe, on the distal portion of which there is mounted a needle coated with a silicone rubber coating, is washed. Then, an elastomeric needle cap is mounted on the needle so as to form an assembly that is subsequently made sterile, preferably by being put into an autoclave.

After the above-mentioned assembly has been in an autoclave, the syringe is filled with its intended liquid and the syringe body is closed by the piston and the plunger that finish off the syringe before it is subsequently packaged.

While in an autoclave, as a result of the elastomeric needle cap being made of a material that is not gas tight (generally rubber), it is possible for pressures to balance between the outside of the elastomeric cap, i.e. the chamber of the autoclave, and the inside of the elastomeric cap, i.e. the housing receiving the needle of the syringe.

During the sterilization cycle in an autoclave, in addition to imparting a temperature increase inside the chamber of the autoclave, a large increase in pressure (e.g. up to 2.3 bars) is also imparted in conventional manner, after establishing one or more partial vacuums in the chamber. The maximum pressure is maintained for a certain period of time (pressure plateau) before imparting a new partial vacuum in the chamber of the autoclave. At the end of the cycle, the pressure is increased to atmospheric pressure, while the temperature drops progressively until it reaches ambient temperature.

From the above-mentioned explanations, it can be understood that during the sterilization cycle in an autoclave, quite sudden pressure changes occur inside the chamber. Thus, during the sudden drop in pressure in the chamber between its maximum pressure value and the partial vacuum, it can happen that the pressure inside the housing within the elastomeric cap cannot balance quickly enough, such that residual pressure occurs momentarily inside the housing at a value that is greater than the value of the pressure existing in the chamber.

In some circumstances, in particular when the lateral wall of the elastomeric cap is not strong enough, the residual pressure present inside the housing generates a deformation of the lateral wall that can lead to the elastomeric cap moving relative to the distal portion of the syringe body on which the cap is mounted. The movement of the cap may even be so great that it may lead to the cap separating from the syringe body when the deformation to which the cap has been subjected prevents the distal portion of the syringe body from being retained in the housing.

In the event of movement between the cap and the syringe body, a break in sealing may occur between the housing inside the cap and the environment outside the cap, thereby running the risk losing sterility in the housing, and thus of losing sterility of the needle. Loss of sterility is established in the event of the cap separating from the syringe body.

Such movement also leads to a risk of liquid being lost from the syringe resulting in the dose of liquid still in the syringe having a volume that has decreased, and in a risk of the user coming into contact with the liquid, which can be dangerous for certain liquids used for examinations, in particular medical imaging. Equally, putting the free end of the needle into contact with the outside environment may give rise to physico-chemical reactions with the liquid, such as crystallization or coagulation, that are likely to degrade the liquid and make the syringe unusable.

The risk of losing sterility is even greater when the syringe body is made of glass, since the use of this material leads to dimensional tolerances occupying a much wider range than for a syringe made of plastics material.

Document EP 1 208 861 proposes a technical solution comprising an annular bead provided with slots, which bead has substantially improved the ability to maintain the needle in a sterile atmosphere that is closed in sealed manner until the needle is used. Nevertheless, there exists a risk of the protection device inflating during sterilization, which may lead to a reduction in the surface area for holding the protection device on the syringe, and thus a risk of separation and of sterility being lost when pressure rises inside the protection device. In addition, when the pressure inside said protection device generates suction, there exists a risk of said device shrinking, which is also likely to interrupt sterility.

Document EP 0 976 415 describes another prior-art device.

An object of the present invention is to provide a syringe-needle protection device that does not present the above-mentioned drawbacks, i.e. that guarantees that the needle in maintained in a sterile atmosphere that is closed in sealed manner until it is used, and in particular that is maintained during the sterilization stage. An object of the present invention is thus to improve the device of document EP 1 208 861.

The present invention thus provides a protection device for protecting a syringe needle, the device comprising an elastomeric needle cap that extends in a generally longitudinal direction and that has a closed distal end and an open proximal end, said cap comprising a lateral wall that extends from said proximal end along a proximal end zone, defining an internal housing for receiving the distal portion of the body of a needle syringe, and an end wall having a thickness that extends from said distal end along a distal end zone, said end wall being suitable for being perforated over a fraction of its thickness by the free end of said needle, said housing comprising, from said proximal end: an opening that presents a maximum diameter; a first segment of frustoconical or circularly cylindrical shape; a circularly-cylindrical second segment that presents a diameter that is less than said maximum diameter, and that is for housing the distal portion of the syringe body that carries said needle; and a third segment that tapers from said second segment towards the end wall of said housing, said lateral wall also being provided with an annular bead that is arranged in said housing between said first and second segments of said housing, at least one slot extending in a longitudinal direction across said annular bead; in which device said second segment includes at least one axial groove that extends longitudinally over a fraction of the height of said second segment.

Advantageously, a plurality of slots, in particular four slots, angularly distributed in regular manner, extend in a longitudinal direction across said bead, and a plurality of grooves, in particular four grooves, angularly distributed in regular manner, extend in a longitudinal direction across said second segment.

Advantageously, said slots are arranged in a staggered configuration with said grooves.

Advantageously, said at least one groove has a width lying in the range 0.1 millimeter (mm) to 0.5 mm and/or a depth of at least 0.1 mm and/or a length that is about 0.5 mm shorter than the length of said second segment, advantageously a length lying in the range 1.50 mm to 1.80 mm, preferably about 1.65 mm.

Advantageously, said third segment includes a preferably-peripheral radially-projecting projection that is adapted to co-operate with said frustoconical intermediate portion of the syringe in the event of suction in the internal housing of the cap, so as to avoid said cap shrinking onto said syringe.

Advantageously, said radially-projecting projection has a radial width lying in the range 0.1 mm to 0.5 mm.

Advantageously, the device further comprises a rigid shell of generally longitudinal and of circularly cylindrical shape, presenting a proximal end that is open and a distal end that is closed at least in part, said shell comprising a longitudinal wall that extends from said proximal end to said distal end and an end wall that is situated at its distal end, said shell being for surrounding and containing said elastomeric needle cap and being provided with retaining means for retaining said cap.

Advantageously, said retaining means include a re-entrant rim that forms the proximal free end of the shell and that presents an inside diameter that is suitable for retaining, in the shell, the proximal end of the lateral wall of the cap.

Advantageously, the proximal end of the outside surface of the lateral wall of the cap includes an annular shoulder that is re-entrant towards the proximal end of the device and that is suitable for co-operating with said annular rim.

Advantageously, said retaining means further include an annular rib that is arranged on the inside face of the longitudinal wall of the shell and that is suitable for co-operating with a first shoulder that is re-entrant towards the distal end of the device and that is situated on the outside surface of the lateral wall of the cap level with the second segment of said housing.

These characteristics and advantages of the present invention, and others, appear more clearly from the following detailed description, given by way of non-limiting example, and with reference to the accompanying drawings, in which:

FIG. 1 is a diagrammatic section view of a needle protection device in an advantageous embodiment of the present invention, showing on the righthand side a prior-art device and on the lefthand side a device of the present invention;

FIG. 2 is a diagrammatic cut-away perspective view showing the protection device of the embodiment of the invention shown in FIG. 1;

FIG. 3 is a view similar to the view in FIG. 2, with the needle protection device assembled on a syringe, around a needle;

FIG. 4 is a view similar to the view in FIG. 2, diagrammatically showing the passage of gas during sterilization.

Figure 5:
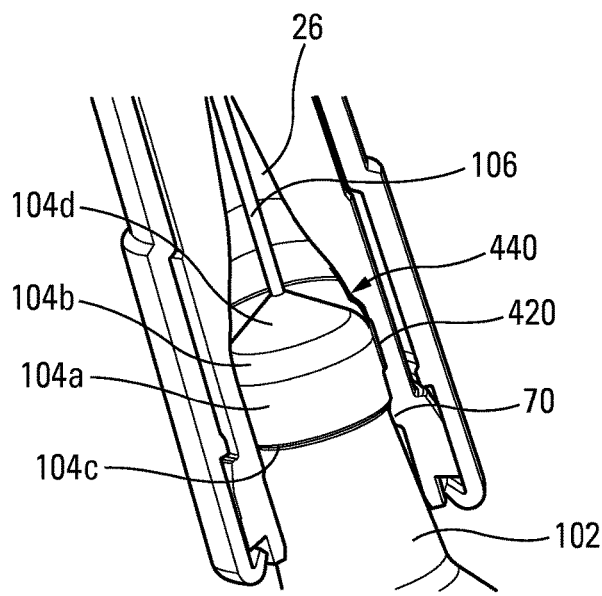
FIG. 5 is a diagrammatic view showing mechanical blocking in the event of increased pressure in the cavity of the protection device of the present invention.

In the following description of the present invention, the adjective "distal" relates to a portion further from the hand of the person holding the syringe, and the adjective "proximal" relates to a portion closer to the hand of the person holding the syringe.

FIG. 1 shows a protection device for protecting a syringe needle, the device being made up of an elastomeric needle cap 20 that extends along a longitudinal direction between an open proximal end 22 and a closed distal end 24. The cap 20 defines an inner housing 26 that is defined by a lateral wall 28 and by an end wall 30.

It should be observed that the righthand portion of FIG. 1 shows the prior-art of document EP 1 208 861, while the lefthand portion of FIG. 1 shows the present invention. It should be observed that there are no differences in the external shape of the cap 20, the differences being present only inside said cap.

In the longitudinal direction along the longitudinal central axis, the lateral wall 28 extends from the proximal end 22 along a proximal end zone 32 that advantageously represents about two thirds of the length of the cap 20.

The end wall 30 is thus solid and, in the longitudinal direction, it extends from the distal end 24 along a distal end zone 34 that advantageously represents about one third of the total length of the cap 20. Thus, the thickness of the end wall 30 (that corresponds to the length of the distal end zone 34) makes it possible to house the free end of the needle of a syringe, as explained below.

As is widespread for this type of needle protection device, the elastomeric cap 20 is circularly cylindrical around its longitudinal central axis. Such circular symmetry relates to the external outline of the cap 20 (lateral wall 28 and end wall 30) and to the internal outline of the lateral wall 28 that defines the housing 26, except for the presence of slots or grooves, as explained below.

The internal housing 26 is made up of a plurality of segments that extend from an opening 36 that is situated at the proximal end 22 of the cap 20, to an end wall 38 that is situated at the other end of the proximal end zone 32.

Adjacent to the opening 36, the housing 26 includes a first segment 40 that presents a circularly-cylindrical shape in the figures, however a frustoconical shape that tapers towards the end wall 38 could also be used.

As shown, the first segment 40 presents a diameter that is substantially equal to the diameter D1 of the opening 36.

At the other end of the opening 36, the above-mentioned first segment 40 is adjacent to a second segment 42 for receiving the distal portion of a syringe body that carries the needle, also known as the hub of the syringe, the second segment presenting a circularly-cylindrical shape, and presenting a diameter D2 that is less than the diameter D1 of the opening 36.

In the opposite direction to the first segment 40, the second segment 42 is extended by a third segment 44 having a diameter that progressively tapers towards the end wall 38 of the housing 26. At the end wall 38 of the housing 26, a circularly-cylindrical fourth segment 46 is formed, presenting a diameter that is substantially equal to the diameter of the syringe needle.

The external outline of the cap 20 presents a shape that is generally circularly cylindrical, with variations in diameter and in shape as described below.

Starting from the distal end 24, where the face of the end wall 30 facing outwards is substantially plane, there extends a frustoconical first portion 50 of relatively limited extent, and a second portion 52 of slightly flared circularly-cylindrical shape that extends to substantially half way up the proximal end zone 32 in the third segment 44 of the housing 26.

In conventional manner, the slightly flared shape of the second portion 52 makes it easier to unmold the cap, and the shape of the first portion 50 makes it easier to center and to mount the rigid shell on the cap, as explained below.

A projecting shoulder 54 connects the second portion 52 to a third portion 56 of very slightly flared circularly-cylindrical shape that extends to the second segment 42 of the housing 26, in the proximity of the first segment 40.

Another projecting shoulder 58 connects the third portion 56 to a fourth portion 60 of frustoconical shape that extends as far as the first segment 40 of the housing 26. The fourth portion 60 is extended towards the proximal end of the cap 20 by a fifth portion 62 of cylindrical shape, itself adjacent to a sixth portion 64 that is set back from the fifth portion 62. The sixth portion 64 includes a shoulder surface 66 that forms an angle that is a little less than 90° relative to the fifth portion 62 and that extends towards the opening 36. Thus, the sixth portion 64 includes an annular shoulder 66 that is re-entrant towards the proximal end 22.

Between the first and second segments 40 and 42 of the housing 26, an annular bead 70 is provided that forms an internal bulge of material at the end of the second segment 42 towards the proximal end 22.

Advantageously, in longitudinal section, the bead 70 presents the shape of half a drop of water having its thicker portion towards the proximal end 22 of the cap 20, the tip of the drop of water joining the second segment 42 level with the other projecting shoulder 58.

The bead 70 defines an internal outline for the housing in the shape of half a pear, and constitutes a mechanical holding rim for the distal portion of the body of the syringe, as explained below. While in an autoclave, the bead 70 improves retention of the distal portion 104 of the syringe 100 in the housing 26.

While in an autoclave, in order to make it easier for water vapor under pressure to pass out from the housing 26, and in order to improve the deformability of the annular bead 70, said annular bead is provided with a plurality of slots 72, advantageously four slots, that extend in a longitudinal direction across the bead 70, the slots being angularly distributed in regular manner.

Naturally, it is possible to provide any number of slots 72 that may be of greater or less depth. If they are numerous, the slots 72 separate between them a large number of portions of the bead 70, each of which forms a small projection. In addition, the slots 72 may be of greater or lesser width.

Naturally, it is possible to provide a bead that presents some other shape (not shown), in particular a shape that is not annular. For example, between two slots 72, the bead may present a bulging internal outline in the shape of a truncated torus having a center that is outside the cap 20.

As can be seen in particular in FIG. 3, which shows a hypodermic syringe 100 in part, the cylindrical body 102 of the syringe is provided with a distal portion 104 that carries the needle 106.

The distal portion 104 presents the general shape of a sphere, made up of a ball carrying the needle 106. More precisely, the distal portion 104 forms an annular bulge that is formed of four portions: a frustoconical end portion 104d that tapers towards the free end of the needle 106; a frustoconical intermediate portion 104b that forms an angle with the frustoconical end portion 104d; a middle portion 104a of shape that is circularly cylindrical; and a frustoconical connection portion 104c. The frustoconical connection portion 104c is adjacent to a circularly-symmetrical portion 108, forming an annular setback 110 relative to the widest portion of the distal portion 104.

As shown in FIG. 3, when the needle 106 penetrates inside the cap 20, the free end of the needle 106 comes to be jabbed in the end wall 30 of the cap 20, while the distal portion 104 of the body 102 of the syringe penetrates into the housing 26 of the cap 20 at the second segment 42.

As can be seen in FIG. 3, after mounting, the annular bead 70 is situated against the frustoconical connection portion 104c, and this provides effective mechanical retention of the distal portion of the syringe 100, formed of the needle 106 and of the cylindrical body 102, inside the housing 26.

As a result of the presence of the annular bead 70 that presses tightly against the frustoconical connection portion 104c, it is not necessary for the diameter D2 of the second segment 42 of the housing 26 to provide a large amount of clamping around the middle portion 104a.

However, the second segment 42 of the housing 26 must be in sealing contact with the middle portion 104a of the distal portion 104 of the syringe, so as to ensure the housing 26 continues to be sterile after being in an autoclave. The sealing in question is microbiological sealing that makes it possible to preserve sterility, i.e. to guarantee the absence of microbial germs or of toxic substances of microbial or fungal origin.

Advantageously, the diameter D2 of the second segment 42 of the housing 26 is greater than or equal to 85%, preferably substantially equal to 92%, of the outside diameter of the distal portion 104 of the syringe body 102. Also advantageously, the minimum inside diameter of the annular bead 70 lies in the range 85% to 95% of the diameter D2 of the second segment 42 of the housing 26, the minimum inside diameter preferably being substantially equal to 90% of the diameter D2 of the second segment 42.

In particular, tests are performed with a 1 milliliter (mL) syringe 100 presenting a syringe body 102 of outside diameter equal to 8.15 mm, the outside diameter of the middle portion 104a being equal to 4.35 mm, while the outside diameter of the frustoconical connection portion 104c is equal to 3.85 mm. For this type of syringe, the cap 20 to be used thus presents the following dimensions:

Diameter of the second segment 42 of the housing 26 (D2): 4 mm; diameter of the housing 26 at the annular bead 70: 3.6 mm; diameter of the opening 36 of the housing 26 (D1): 4.7 mm.

The above-mentioned dimensions are given for a cap 20 presenting a total length of 23.5 mm for an outside diameter of 7 mm in the fifth portion 62, the fourth portion 60 tapering to a minimum outside diameter of 6.5 mm.

Naturally, the dimensions of the cap depend on the dimensions of the syringe, and in particular of its distal portion carrying the needle.

In an autoclave, the sealing of the housing 26 of such a cap is improved by limiting the risks of movement between the cap 20 and the distal portion 104 of the syringe. Specifically, the annular bead 70 guarantees that the distal portion 104 of the syringe is mechanically blocked in the second segment 42 of the housing 26 while in an autoclave. Furthermore, the sealed contact provided by the second segment 42 of the housing 26 against the middle portion 104a of the distal portion 104 of the syringe generates microbiological sealing between the housing 26 and the outside of the protection device after being in an autoclave, and this guarantees that the housing and the needle remain sterile until the syringe 100 is used, or more precisely until the cap 20 is separated from the needle 106.

In the invention, said second segment 42 includes at least one axial groove 420 that extends longitudinally across a fraction of the height of said second segment 42. As can be seen in the figures, this at least one axial groove 420 is rectilinear. Preferably, there are four axial grooves 420 that and angularly distributed in regular manner, and that are arranged in a staggered configuration relative to the slots 70.

Figure 7:
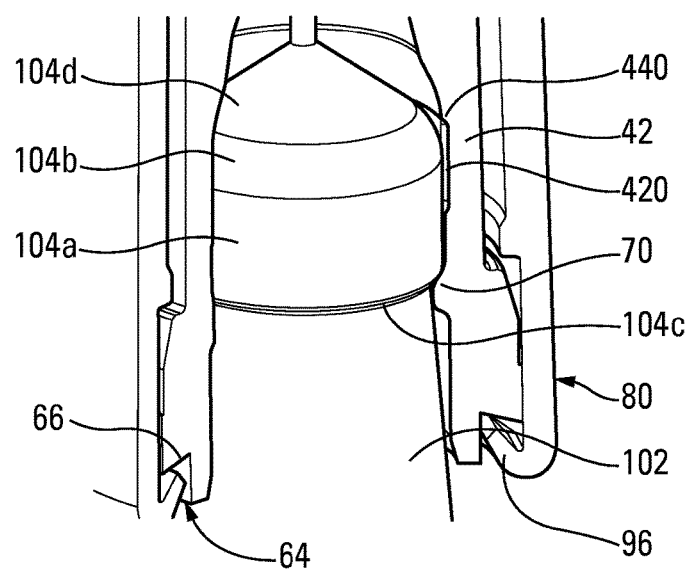
FIG. 7 is a diagrammatic view showing the limited inflation with the device of the present invention.
Figure 8:
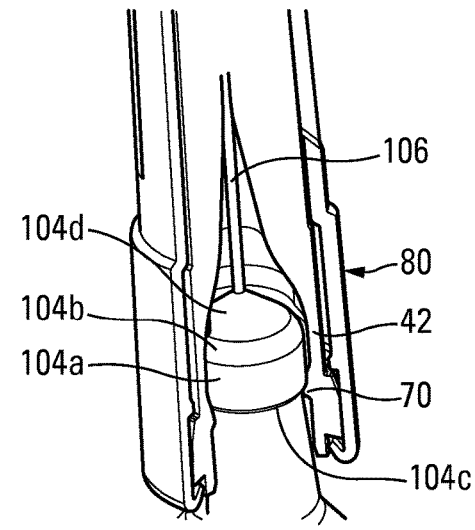
FIG. 8 is a view similar to the view in FIG. 7, showing the greater inflation with a device of the prior art.

The grooves enable air to pass during vapor sterilization, as represented diagrammatically in FIG. 4, thereby making it possible to avoid excessive inflation of the second segment as shown in FIG. 8, likely to cause the bead 70 to disengage from the syringe. Specifically, in the absence of the axial grooves 420 of the invention, inflation of the second segment 42 in the event of increased pressure in the housing 26 decreases the contact zone between the bead 70 and the frustoconical connection portion 104c, as can be seen in FIG. 8. Since the increased pressure tends to deform the second segment 42 radially outwards, the bead 70 no longer suffices to hold the cap in position on the syringe. With the presence of the grooves 420 of the invention, such inflation is greatly reduced, as shown in FIG. 7, and consequently the risks of disengagement are greatly reduced, or even eliminated.

In order to guarantee sealing and sterility, said axial grooves 420 must extend longitudinally over a fraction only of the height of said second segment 42. Advantageously, each axial groove 420 presents at least one of the following characteristics: a width lying in the range 0.1 mm to 0.5 mm; a depth of at least 0.1 mm; a length that is about 0.5 mm shorter than the length of said second segment 42, advantageously a length lying in the range 1.50 mm to 1.80 mm, preferably about 1.65 mm. Naturally, the dimensions also depend on the dimensions of the syringe, and in particular of its distal portion carrying the needle.

Figure 6:
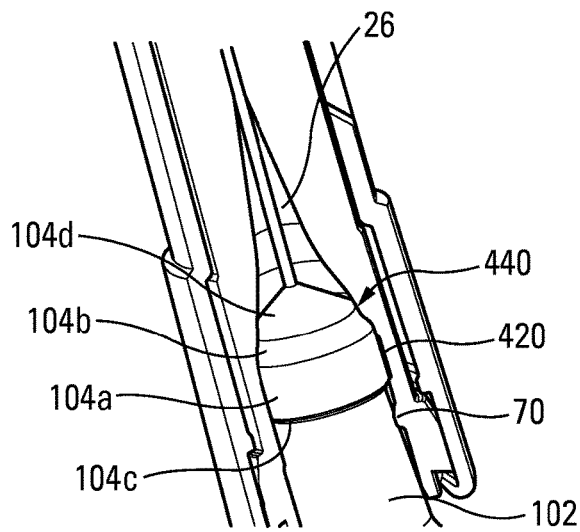
FIG. 6 is a view similar to the view in FIG. 5, showing mechanical blocking in the event of suction in the cavity of the protection device of the present invention.

Advantageously, said third segment 44 of the cap includes a radially-projecting projection 440, preferably peripheral, that is adapted to co-operate with said frustoconical intermediate portion 104b of the syringe 100 in the event of suction in the internal housing 26 of the cap 20. In particular, this makes it possible to limit the degree to which said cap 20 shrinks onto said syringe 100 in the event of suction in the internal housing 26 of the cap, in particular during sterilization. FIG. 6 shows such a situation of suction in the housing 26, with the bead 70 axially offset a little from the frustoconical connection portion 104c, the shrinkage of the cap being limited by the radially-projecting projection 440 that comes to co-operate with said frustoconical intermediate portion 104b of the syringe.

Advantageously, said radially-projecting projection 440 has a radial width lying in the range 0.1 mm to 0.5 mm, i.e. it extends radially inwards by this distance, starting from the inside surface of the third segment 44. FIG. 1, which compares a cap of the invention (on the left) with a cap of document EP 1 208 861, shows that the height of the second segment 42 has been reduced so as to provide said radially-projecting projection 440 at the junction between said second and third segments 42 and 44.

As shown in particular in FIGS. 2 and 3, the present invention also provides a syringe-needle protection device that, in addition to the above-mentioned elastomeric cap 20, includes a rigid shell 80 in which the cap 20 is housed.

This type of shell 80 is conventionally used to reinforce the protection of the user of the syringe against being pricked by the needle, by offering rigid external additional protection that is difficult to perforate by the needle 106.

The rigid shell 80 presents a generally longitudinal circularly cylindrical shape, it is mounted in coaxial manner relative to the cap 20, and it extends between an open proximal end 82 and a closed distal end 84.

The rigid shell 80 is dimensioned to enable the cap 20 to be inserted and blocked therein. To this end, the cavity 86 defined by the internal outline of the rigid shell 80 presents a shape that substantially matches the external shape of the cap 20.

The rigid shell 80 is made up of a longitudinal wall 88 that extends from the proximal end 82 to the distal end 84 where the longitudinal wall 88 is extended by an end wall 92 that closes the cavity 86.

Between the end wall 92 and about two-fifths of the length of the longitudinal wall 88, said longitudinal wall may be provided with four cutouts 94 so as to enable water vapor under pressure to pass from the chamber of the autoclave to the housing 26.

The four cutouts 94 are of generally longitudinal shape and they are radially distributed at 90° from one another.

In order to retain the cap 20 inside the cavity 86 of the rigid shell 80, cap-retaining means are provided including a re-entrant rim 96, preferably an annular rim, that forms an element, preferably a collar, projecting towards the inside of the cavity 86.

The re-entrant rim 96 is thus housed in the step formed by the sixth portion 64 of the external outline of the cap 20, so that the cap 20 is prevented from leaving the shell 80 by the re-entrant rim 96 coming into axial abutment against the shoulder surface 66.

During mounting, when the cap 20 is fully driven into the shell 80, the essentially plane outside face of the end wall 30 of the cap 20 comes into axial abutment against the inside face of the end wall 92 of the shell 80. However, in the normal position, there is no contact between the outside face of the end wall 30 of the cap 20 and the inside face of the end wall 92 of the shell 80.

Furthermore, in order to block relative longitudinal movement in translation between the cap 20 and the rigid shell 80, more particularly movement of the cap 20 towards the end wall 92 of the shell 80, an annular rib 98 is provided as complementary retaining means, which annular rib is arranged on the inside face of the longitudinal wall 88 of the shell 80. The annular rib 98 is suitable for co-operating with the outside face of the lateral wall 28 of the cap 20 by coming into abutment against the shoulder 58 of the cap 20.

The shoulder 58 forms a first shoulder that is re-entrant towards the distal end 24 of the device, this first shoulder 58 being situated on the outside face of the lateral wall 28 of the cap 20 level with the second segment 42 of the housing 26.

As can be seen in FIG. 2, approximately mid-way along the shell 80, the longitudinal wall 88 includes an annular shoulder 99 at least on its outside face, and preferably over the entire thickness of the longitudinal wall 88 of the shell 80 (as shown), which annular shoulder 99 is re-entrant towards the distal end 24 of the device (the inside diameter of the cavity 86 being smaller on the side of the shoulder 99 that is situated closest to the end wall 92).

The re-entrant shoulder 99 is formed so as to be situated facing the shoulder 54 of the cap 20, which shoulder 54 forms a second shoulder that is re-entrant towards the distal end of the device, being situated on the outside face of the lateral wall 28 of the cap 20 level with the third segment 44 of the housing 26.

As can be seen in FIG. 2, the re-entrant shoulder 99 may be situated both on the inside face and on the outside face of the longitudinal wall 88, so as to form an annular step of the wall.

In particular, the purpose of the annular shoulder 99 is to make it easier for the various machines of the manufacturing and assembly line to handle the needle protection device.

Furthermore, when the cap 20 is inserted inside the cavity 86 of the shell 80, contact exists between the fifth portion 62 of the external outline of the cap 20, and the inside face of the longitudinal wall 88, situated between the rib 98 and the rim 96.

When the distal portion 104 of the body 102 of the syringe is inserted into the housing 26, the annular bead 70 is flattened by the distal portion 104 of the body 102 of the syringe. Since the lateral wall 28 of the cap is made of a material that is sufficiently flexible (e.g. of rubber), a portion of the deformation is absorbed by the slots 72.

In addition, since the lateral wall 28 of the cap presents a thickness that is sufficiently thin relative to the fourth portion 60 of the external outline of the cap 20, deformation of the annular bead 70 causes the lateral wall 28 to move radially outwards at this location, resulting in deformation of the fourth portion 60 that moves closer to the inside face of the longitudinal cylindrical wall 88 of the shell 80: this is made possible as a result of the external frustoconical shape of the fourth portion 60 of the lateral wall 28 that is situated level with the annular bead 70, and as a result of the annular gap that is available on the inside face of the longitudinal wall 88 of the shell 80 level with the fourth portion 60.

Naturally, the fourth portion 60 could also present a frustoconical shape that is the other way round compared to the shape shown, i.e. a shape that tapers towards the proximal end 22 of the cap.

The fourth portion 60 could also present a shape that is different from frustoconical, provided that once the cap is housed in the shell, the surface generates a free annular gap between it and the facing zone of the longitudinal wall 88 of the rigid shell 80. Specifically, the annular gap makes it possible to receive a portion of the radially-outward deformation of the zone of the lateral wall 28 of the cap 20 that is situated against the middle portion 104a of the distal portion 104 of the syringe.

More generally, there preferably exists a gap, advantageously an annular gap, between the longitudinal wall 88 of the rigid shell 80 and the lateral wall 28 of the cap 20, that extends in longitudinal manner from the cutouts 94 to the annular rib 98 arranged on the inside face of the longitudinal wall 88 of the shell 80, i.e. to the projecting shoulder 58, on either side of the shoulder 99. The gap enables water vapor under pressure to pass from the chamber of the autoclave to the housing 26 as a result of the material constituting the cap 20 being permeable to gas, in particular to water vapor under pressure. Furthermore, the portion of the gap that surrounds the second segment 42 of the housing 26 also makes it possible to receive the radial expansion of the zone of the lateral wall 28 of the cap 20 that surrounds the middle portion 104a of the distal portion 104 of the syringe.

Thus, it should be understood that the presence of the shell does not modify in any way the use and the operation of the cap 20 for sterilization while in an autoclave and for maintaining the sterility of the syringe 106 after being in an autoclave. Furthermore, the presence of the shell does not modify the force opposing separation while separating the cap 20 from the syringe 100, but it increases the safety of the user against being pricked.

Although the present invention is described above with reference to an embodiment, naturally the present invention is not limited by that embodiment, and, on the contrary, any useful modification could be applied thereto by the person skilled in the art, without going beyond the ambit of the present invention, as defined by the accompanying claims.

The invention claimed is:

1. A protection device for protecting a syringe needle, the protection device comprising an elastomeric needle cap that extends in a generally longitudinal direction and that has a closed distal end and an open proximal end, said cap comprising a lateral wall that extends from said proximal end along a proximal end zone, defining an internal housing for receiving a distal portion of a body of a needle syringe, and an end wall having a thickness that extends from said distal end along a distal end zone, said end wall being suitable for being perforated over a fraction of the thickness of the end wall by a free end of the syringe needle, said housing comprising, from said proximal end:
an opening that presents a maximum diameter;
a first segment of frustoconical or circularly cylindrical shape;
a circularly-cylindrical second segment that presents a diameter that is less than said maximum diameter, and that is for housing the distal portion of the syringe body that carries said syringe needle; and
a third segment that tapers from said second segment towards the end wall of said housing, said lateral wall also being provided with an annular bead that is arranged in said housing between said first segment and said second segment of said housing, at least one slot extending in a longitudinal direction across said annular bead;

wherein said second segment includes at least one axial groove formed in an interior wall portion of the second segment facing an inside of the housing and that does not extend radially through an entire thickness of the interior wall portion of the second segment, the at least one axial groove that is limited to said second segment and that extends longitudinally over a fraction of the height of said second segment so as to allow air to pass through the at least one axial groove during vapor sterilization of the needle syringe when fully inserted in the protection device such that the annular bead mechanically retains the housing to the distal portion of the body by engaging a corresponding connection portion of the body, and wherein the at least one axial groove allows air to pass through during vapor sterilization of the needle syringe while the annular bead maintains the housing retained to the distal portion of the body through engagement with the connection portion.

2. The device according to claim 1, wherein a plurality of slots, angularly distributed in regular manner, extend in a longitudinal direction across said bead, and a plurality of said at least one axial groove, angularly distributed in regular manner, extend in a longitudinal direction across said second segment.

3. The device according to claim 2, wherein said slots are arranged in a staggered configuration with said plurality of said at least one axial groove.

4. The device according to claim 2, wherein the plurality of slots number four and the plurality of said at least one axial groove number four.

5. The device according to claim 1, wherein said at least one groove has a width lying in the range 0.1 mm to 0.5 mm and/or a depth of at least 0.1 mm and/or a length that is about 0.5 mm shorter than the length of said second segment.

6. The device according to claim 1, wherein said third segment includes a peripheral radially-projecting projection that is adapted to co-operate with a frustoconical intermediate portion of the needle syringe in the event of suction in the internal housing of the cap, so as to avoid said cap shrinking onto said needle syringe.

7. The device according to claim 6, wherein said radially-projecting projection has a radial width lying in the range 0.1 mm to 0.5 mm.

8. The device according to claim 1, further including a rigid shell of generally longitudinal and of circularly cylindrical shape, presenting a proximal end that is open and a distal end that is closed at least in part, said shell comprising a longitudinal wall that extends from said proximal end of the shell to said distal end of the shell and an end wall that is situated at said distal end of the shell, said shell being for surrounding and containing said elastomeric needle cap and being provided with retaining structures for retaining said cap.

9. The device according to claim 8, wherein said retaining structures include a re-entrant rim that forms the proximal end of the shell and that presents an inside diameter that is suitable for retaining, in the shell, a proximal end of the lateral wall of the cap.

10. The device according to claim 9, wherein the proximal end of the outside surface of the lateral wall of the cap includes an annular shoulder that is re-entrant towards the proximal end of the cap and that is suitable for co-operating with said re-entrant rim.

11. The device according to claim 8, wherein said retaining structures further include an annular rib that is arranged on an inside face of the longitudinal wall of the shell and that is suitable for co-operating with a first shoulder that is re-entrant towards the distal end of the cap and that is situated on an outside surface of the lateral wall of the cap level with the second segment of said housing.

12. The device according to claim 1, comprising a plurality of said at least one axial groove that are angularly distributed about an axis of said second segment.

13. A needle syringe assembly, comprising the protection device of claim 1 and a needle syringe on which the protection device is mounted, wherein, in an assembled position, a distal portion of a body of the needle syringe is received in the circularly-cylindrical second segment such that the at least one axial groove extending longitudinally over the fraction of the height of the second segment allows air to pass through the at least one axial groove during vapor sterilization of the needle syringe in the assembled position.

14. The needle syringe assembly according to claim 13, wherein the annular bead mechanically retains the housing to the distal portion of the body by engaging the corresponding connection portion of the body, and wherein the at least one axial groove allows air to pass through during vapor sterilization of the needle syringe while the annular bead maintains the housing retained to the distal portion of the body through engagement with the connection portion.

15. A needle syringe assembly, comprising a needle syringe and a protection device removably mounted on the needle syringe for protecting a needle of the needle syringe, wherein the protection device comprises an elastomeric needle cap that extends in a generally longitudinal direction and that has a closed distal end and an open proximal end, said cap comprising a lateral wall that extends from said proximal end along a proximal end zone, defining an internal housing for receiving a distal portion of a body of the needle syringe, and an end wall having a thickness that extends from said distal end along a distal end zone, said end wall being suitable for being perforated over a fraction of a thickness of the end wall by the free end of the needle, said housing comprising, from said proximal end:

an opening that presents a maximum diameter;

a first segment of frustoconical or circularly cylindrical shape;

a circularly-cylindrical second segment that presents a maximum diameter that is less than said maximum diameter of the opening, and that is for housing the distal portion of the syringe body that carries said needle; and a third segment that tapers from said second segment towards the end wall of said housing, said lateral wall also being provided with an annular bead that is arranged in said housing between said first segment and said second segment of said housing, and at least one slot extending in a longitudinal direction across said annular bead;

wherein said second segment includes at least one axial groove formed in an interior wall portion of the second segment facing an inside of the housing and that does not extend radially through an entire thickness of the interior wall portion of the second segment, the at least one axial groove that is limited to said second segment and that extends longitudinally over a fraction of the height of said second segment so as to allow air to pass through the at least one axial groove during vapor sterilization of the needle syringe when fully inserted in the protection device, such that the annular bead mechanically retains the housing to the distal portion of the body by engaging a connection portion of the distal portion of the body, and wherein the at least one axial groove allows air to pass through during vapor sterilization of the needle syringe while the annular bead remains engaged with the connection portion of the distal portion of the body.

16. The needle syringe assembly according to claim 15, wherein the connection portion of the distal portion of the body has a frustoconical shape.

17. The needle syringe assembly according to claim 15, wherein each of the at least one axial groove is circumferentially offset relative to each of the at least one slot.

18. The device according to claim 5, wherein said at least one groove has the length lying in the range 1.50 mm to 1.80 mm.

19. The device according to claim 18, wherein said at least one groove has the length of 1.65 mm.

\* \* \* \* \*